US007879344B2

(12) United States Patent
Feldkamp et al.

(10) Patent No.: US 7,879,344 B2
(45) Date of Patent: Feb. 1, 2011

(54) TRANSDERMAL DELIVERY OF OLEOCANTHAL FOR RELIEF OF INFLAMMATION

(75) Inventors: Joseph R. Feldkamp, Appleton, WI (US); David William Koenig, Menasha, WI (US); Scott W. Wenzel, Neenah, WI (US); Wael Joseph, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 987 days.

(21) Appl. No.: 11/427,663

(22) Filed: Jun. 29, 2006

(65) Prior Publication Data

US 2008/0003273 A1 Jan. 3, 2008

(51) Int. Cl.
*A61K 9/00* (2006.01)
(52) U.S. Cl. ...................................... 424/400; 424/449
(58) Field of Classification Search ........................ None
See application file for complete search history.

(56) References Cited

U.S. PATENT DOCUMENTS

| 4,405,616 | A | * | 9/1983 | Rajadhyaksha | .............. | 514/788 |
| 5,026,556 | A | * | 6/1991 | Drust et al. | .................. | 424/449 |
| 5,976,566 | A | | 11/1999 | Samour et al. | | |
| 6,083,996 | A | | 7/2000 | Buyuktimkin et al. | | |
| 6,391,290 | B1 | * | 5/2002 | Fowler | .......................... | 424/59 |
| 2003/0082226 | A1 | | 5/2003 | Samour et al. | | |
| 2004/0180066 | A1 | | 9/2004 | Lee et al. | | |
| 2007/0000021 | A1 | | 1/2007 | Yang et al. | | |
| 2007/0299129 | A1 | * | 12/2007 | Sauniere et al. | .............. | 514/448 |
| 2008/0003273 | A1 | | 1/2008 | Feldkamp et al. | | |
| 2009/0076142 | A1 | * | 3/2009 | Han et al. | .................... | 514/532 |

FOREIGN PATENT DOCUMENTS

| FR | 2864447 | A1 | 7/2005 |
| GB | 2236250 | A | 4/1991 |
| WO | 0072883 | A2 | 12/2000 |
| WO | 2006122128 | A2 | 11/2006 |
| WO | 2007081808 | A2 | 7/2007 |
| WO | WO 2007133908 | A2 | * 11/2007 |

OTHER PUBLICATIONS

Andrewes, P., et al., "Sensory Properties of Virgin Olive Oil Polyphenols: Identification of Deacetoxy-ligstroside Aglycon as a Key Contributor to Pungency," J. Agric. Food Chem., vol. 51, pp. 1415-1420 (2003).
Beauchamp, et al., "Ibuprofen-like activity in extra-virgin olive oil," Nature, vol. 437, pp. 45-46, Sep. 1, 2005.
Bronaugh, et al., eds., "Percutaneous Absorption" in Mechanisms-Methodology-Drug Delivery, 2nd Ed., Marcel Dekker, Inc., 1989, pp. 567-593.
Chan, T., "Percutaneous penetration enhancers: An update," Proceedings of the 9th Biennial International Conference of Perspectives in Percutaneous Penetration, Jan. 2005, pp. 18-22.
Feldkamp. J., et al., "Interactions of Binary Solvents with Charged Expandable CLays. 1. Theory", J. Phys. Chem., 1994, 98, pp. 13594-13600.
Fujita, A., "Prediction of Organic Compounds by a Conceptual Diagram," Pharmaceutical Bulletin, Tokyo Pharmaceutical Society of Japan, vol. 2, No. 2, p. 163-173 (1954).
Tripoli, E., et al., "The phenolic compounds of olive oil: structure, biological activity and beneficial effects on human health", Nutrition Research Reviews, Jun. 2005, vol. 18, No. 1, pp. 98-112.
Smith, et al., "Percutaneous Penetration Enhancers," CRC Press, 1st Ed., 1995, p. 7-8.
Smith, III, et al., "Synthesis and Assignment of Absolute Configuration of (−)-Oleocanthal: A Potent, Naturally Occurring Non-steroidal Anti-inflammatory and Anti-Oxidant Agent Derived from Extra Virgin Olive Oils," Org. Lett., vol. 7 (22), pp. 5075-5078 (2005).
Symrise, "Dihydroavenanthramide D for topical applications to help reduce itch and irritation," http://pressroom.symrise.com/en/pressemeldungen/pm141205.php, Dec. 14, 2005.
Weintraub, A., "Of Oil and Rare Diseases," BusinessWeek, vol. 3951, p. 81, Sep. 19, 2005.
Owen, et al., "The antioxidant/anticancer potential of phenolic compounds isolated from olive oil," European Journal of Cancer, 2000, vol. 36, pp. 1235-1247.
International Search Report and Written Opinion from PCT/IB2007/052071, dated Dec. 6, 2007.
Smith, III, et al., J. Org. Chem., vol. 72, pp. 6891-6900 (2007).
Non-final Office action, U.S. Appl. No. 11/938,596 (dated Mar. 26, 2009).
Goodman and Gilman's "The Pharmacological Basis of Therapeutics," edited by Joel G. Hardman and Lee E. Limbird, The McGraw-Hill Companies, Inc., p. 54-56 (2001).
Remington's "The Science and Practice of Pharmacy," 20th edition, edited by Daniel Limmer, University of the Sciences in Philadelphia, p. 841-42, 845-46 (2000).
International Search Report and Written Opinion issued Aug. 21, 2009 for PCT/IB2008/054678.
Impellizzeri, et al., "A Simple High-Performance Liquid Chromatography Method for the Determination of Throat-Burning Oleocanthal with Probated Antiinflammatory Activity in Extra virgin Olive Oils," J. Agric. Food Chem., vol. 54, pp. 3204-3208 (Apr. 8, 2006).
Final Office action issued for U.S. Appl. No. 11/938,596 (Sep. 29, 2009).

* cited by examiner

*Primary Examiner*—Robert A Wax
*Assistant Examiner*—Melissa S Mercier
(74) *Attorney, Agent, or Firm*—Armstrong Teasdale LLP

(57) ABSTRACT

The present disclosure generally relates to compositions for reducing inflammation, and more particularly, to compositions comprising oleocanthal. The oleocanthal-containing compositions are particularly suitable for transdermal delivery. The compositions may also be used in combination with personal care products, such as wipes and absorbent articles, and may be incorporated into transdermal patches.

17 Claims, No Drawings

TRANSDERMAL DELIVERY OF OLEOCANTHAL FOR RELIEF OF INFLAMMATION

BACKGROUND OF DISCLOSURE

The present disclosure generally relates to methods and compositions for reducing inflammation, and more particularly, to compositions comprising oleocanthal. The oleocanthal-containing compositions are particularly suitable for transdermal delivery.

Topical routes of drug administration are often desirable because problems associated with other drug delivery means can be avoided. For instance, oral administration of drugs is often associated with variable absorption and metabolism of the drug and gastrointestinal irritation. In particular, the gastrointestinal irritation associated with the oral administration of non-steroidal anti-inflammatory drugs (NSAIDs), such as aspirin, ibuprofen, and naproxen, among others, is well documented. In an effort to overcome the drawbacks of oral administration of NSAIDs, an ibuprofen based cream was recently introduced that can be applied directly to skin above the source of inflammation. Although such a cream may avoid some of the traditional problems associated with administration of NSAIDs (e.g., gastrointestinal irritation), there are other problems associated with transdermal administration of these drugs.

For instance, the skin provides a protective barrier against foreign materials and infections and helps protect the body from water loss. The layer of skin primarily responsible for this barrier function is the epidermis, and more particularly, the uppermost layer of the epidermis (i.e., the stratum corneum or horny layer). In mammals, the stratum corneum consists of horny skin cells (i.e., corneocytes) embedded in a lipid matrix. This structure is often referred to as a "brick and mortar" model, with the corneocytes being the "bricks" and the epidermal lipids being the "mortar." The structure of the stratum corneum provides a strong barrier to the diffusion of molecules through the skin, often restricting diffusion through the skin to molecules having a certain size, solubility, and/or lipophilicity. This presents a problem for the diffusion of certain NSAIDs, such as ibuprofen, which have a relatively low solubility in fats and oils, and under certain conditions may precipitate and form an insoluble salt.

There is thus a need for compositions useful for the relief of inflammation that may be effectively delivered transdermally.

SUMMARY OF THE DISCLOSURE

The present disclosure is directed to compositions, such as gels, lotions, suspensions, creams, and sprays, that are suitable for topical application. More particularly, the compositions comprise oleocanthal, and may be used for the relief of inflammation and pain in users. The compositions may also be used in combination with personal care products, such as wipes and absorbent articles, and may be incorporated into transdermal patches. Advantageously, the oleocanthal-containing compositions more readily penetrate through the stratum corneum, as compared to compositions comprising traditional NSAIDs.

In one aspect, the present disclosure is directed to a topical composition for relief of inflammation. The topical composition comprises a pharmaceutically acceptable carrier and at least about 0.04% (by weight of the composition) of oleocanthal.

In another aspect, the present disclosure is directed to a topical composition for relief of inflammation, the topical composition comprising a pharmaceutically acceptable carrier, oleocanthal, and a skin penetration enhancer.

In still another aspect, the present disclosure is directed to a transdermal patch. The patch comprises a backing layer and a reservoir layer, wherein the reservoir layer comprises a composition comprising an amount of oleocanthal, a skin penetration enhancer, and fibers.

Other objects and features will be in part apparent and in part pointed out hereinafter.

DETAILED DESCRIPTION OF THE DISCLOSURE

In accordance with the present disclosure, it has been discovered that oleocanthal can be delivered transdermally for relief of inflammation and/or pain. More particularly, oleocanthal can be introduced into various compositions, such as gels, lotions, suspensions, creams, and sprays, or transdermal patches, which may be topically applied at the source of inflammation. Advantageously, the oleocanthal-containing compositions overcome several of the drawbacks associated with topical formulations containing other NSAIDs as active ingredients.

Certain types of olive oil, and in particular extra virgin olive oil, have been shown to contain a naturally occurring compound that acts in a similar manner to traditional NSAIDs in the relief of inflammation and pain. The compound, called oleocanthal, is generally thought to be responsible for the stinging sensation produced in the throat when certain olive oils are ingested, and is believed to inhibit the activity of the cyclooxygenase-1 (COX-1) and cyclooxygenase-2 (COX-2) enzymes. Because the inhibition of COX-1 and COX-2 enzymes underlies the anti-inflammatory actions of ibuprofen and other NSAIDs, oleocanthal can advantageously be used in a manner similar to other NSAIDs to relieve inflammation and pain. Oleocanthal has the following chemical structure:

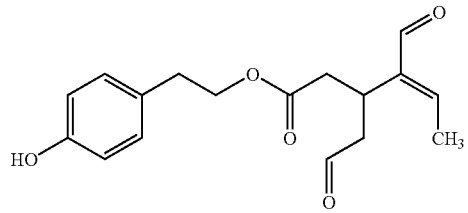

Traditionally, it has been difficult to administer ibuprofen and other similar NSAIDs transdermally. Ibuprofen is known to have a relatively low solubility in fats and oils, and has a tendency to precipitate at higher pHs. This is particularly problematic for transdermal administration, given the high concentration of lipids in the stratum corneum. Consequently, formulating a transdermal ibuprofen-containing composition that is capable of penetrating through the stratum corneum in effective amounts is difficult.

In accordance with the present disclosure, it has been discovered that oleocanthal does not suffer from the same drawbacks as ibuprofen, when administered transdermally. More particularly, oleocanthal is readily highly soluble in fats and oils, and remains in its neutral state over a broad pH range. Without wishing to be bound to any particular theory, it is believed that the ability of oleocanthal to remain in a neutral state over a broad pH range contributes to the ability of oleocanthal to more readily penetrate the stratum corneum, as compared to ibuprofen and similar NSAIDs. For instance, compounds will generally exhibit better penetration when in a neutral, or non-ionized, state. Since the phenolic group in the structure of oleocanthal generally does not begin to ionize until about pH 9.5, oleocanthal will typically remain in its neutral, non-ionized form in compositions having a pH up to about 9.5. This is advantageous for transdermal delivery. Since most transdermal compositions are formulated to have a pH of from about 3.5 to about 8.5, and more typically from about 5.0 to about 6.0, oleocanthal will mostly be in its neutral, non-ionized state when the transdermal composition is contacted with skin. In contrast, ibuprofen and similar NSAIDs, which contain a carboxylic acid group that may begin to ionize at a pH of about 4.0, will be all or partly in their ionized state (and thus insoluble) when the transdermal composition is contacted with skin. Consequently, oleocanthal penetrates the stratum corneum more readily than ibuprofen and other similar NSAIDs.

Thus, in one aspect, the present disclosure is directed to compositions for the relief of inflammation and/or pain, wherein the compositions comprise an effective amount of oleocanthal. Advantageously, the compositions may be topically applied at the source of inflammation and/or pain. In particular, the compositions are useful for reducing skin, joint, and muscle inflammation.

Oleocanthal may be prepared and applied transdermally in any suitable form, but preferably is prepared in forms including, without limitation, aqueous solutions, gels, balms, lotions, suspensions, creams, milks, salves, ointments, sprays, emulsions, oils, resins, foams, solid sticks, aerosols, and the like. Specific examples of products the oleocanthal may be incorporated into include foot creams and wraps, topical analgesics, sunburn relief gels and creams, suntan lotions, insect bite relief sprays and/or lotions, diaper rash creams, anti-irritation or anti-inflammatory creams, oily or oily-alcoholic lotions, oily-alcoholic, oily-aqueous, or aqueous-alcoholic gels, and the like.

In another aspect, the oleocanthal-containing compositions may be incorporated into personal care products, such as wipes, absorbent articles, bath tissues, cloths, and patches among others. More particularly, the oleocanthal may be incorporated into wipes such as wet wipes, dry wipes, hand wipes, face wipes, cosmetic wipes, and the like, absorbent articles including medical wraps and bandages, patches such as eye patches and dermal patches, cloth material such as spa gloves and socks, headbands, wristbands, helmet pads, and the like.

The oleocanthal used in the compositions described herein may be obtained from any suitable source. For instance, oleocanthal can be extracted from certain olive oils, such as extra virgin olive oil, using any suitable procedure known in the art, such as that described in Andrewes, et al., J. Agric. Food Chem., Vol. 51, No. 5, pp. 1415-1420 (2003). More specifically, in this procedure 200 g of olive oil is dissolved in 400 mL of hexane and extracted with 400 mL of a 60:40 ethanol:water mixture for 2 minutes. The aqueous ethanol/water phase is collected and washed with a second 400 mL volume of hexane. The hexane phase is discarded and the ethanol/water phase is rotary evaporated to dryness using a water bath at 40° C. The dried extract, which contains a number of olive oil components, may then be further separated using chromatographic means, such as high performance liquid chromatography (HPLC). Alternately, the oleocanthal may be synthesized using any suitable procedure, such as that described in Smith, et al., Org. Lett., Vol. 7, No. 22, pp. 5075-5078 (2005).

Although extra virgin olive oil can comprise up to 0.2 g/L of oleocanthal, or about 0.02 wt. % or less oleocanthal, at these concentrations, oleocanthal generally has little to no effect on reducing inflammation. In contrast, the compositions of the present disclosure advantageously comprise oleocanthal in an amount effective to reduce inflammation and/or pain. Preferably, the compositions comprise at least about 0.04% (by weight of the composition) of oleocanthal. More preferably, the compositions comprise from about 0.04% (by weight of the composition) to about 10.0% (by weight of the composition) of oleocanthal, more preferably from about 0.10% (by weight of the composition) to about 5.0% (by weight of the composition) of oleocanthal, and still more preferably about 0.50% (by weight of the composition) of oleocanthal.

In addition to oleocanthal, the oleocanthal-containing compositions of the present disclosure may also include a skin penetration enhancer or mixture of skin penetration enhancers in order to increase the permeability of oleocanthal into the skin. More particularly, skin penetration enhancers help to improve transport of oleocanthal into the blood stream by assisting in the penetration of the oleocanthal through the skin's stratum corneum. This may be accomplished by a number of different mechanisms including, for example, by extracting lipids from the stratum corneum, increasing the partitioning of the oleocanthal into the skin, and disrupting the lipid bilayer of the stratum corneum, thus rendering the stratum corneum structure more fluid and increasing the ability of the oleocanthal to diffuse through the stratum corneum.

Examples of suitable skin penetration enhancers include sulfoxides, alcohols, fatty acids, fatty acid esters, polyols, amides, surfactants, terpenes, alkanones, and organic acids, among others.

Specific examples of suitable sulfoxides include dimethylsulfoxide (DMSO) and decylmethylsulfoxide, among others.

Suitable alcohols include alkanols such as ethanol, propanol, butanol, pentanol, hexanol, octanol, n-octanol, nonanol, decanol, 2-butanol, 2-pentanol, and benzyl alcohol; fatty alcohols, such as caprylic alcohol, decyl alcohol, lauryl alcohol, 2-lauryl alcohol, myristyl alcohol, cetyl alcohol, stearyl alcohol, oleyl alcohol, linoleyl alcohol, and linolenyl alcohol; and isopropyl alcohol.

Examples of suitable fatty acids include linear fatty acids such as valeric acid, heptanoic acid, pelagonic acid, caproic acid, capric acid, lauric acid, myristic acid, stearic acid, oleic acid, and caprylic acid; and branched fatty acids, such as isovaleric acid, neopentanoic acid, neoheptanoic acid, neononanoic acid, trimethyl hexanoic acid, neodecanoic acid, and isostearic acid.

Examples of suitable fatty acid esters include aliphatic fatty acid esters such as isopropyl n-butyrate, isopropyl n-hexanoate, isopropyl n-decanoate, isopropyl myristate, isopropyl palmitate, and octyldodecyl myristate; alkyl fatty acid esters such as ethyl acetate, butyl acetate, methyl acetate, methylvalerate, methylpropionate, diethyl sebacate, and ethyl oleate; and diisopropyl adipate and dimethyl isosorbide.

Examples of suitable polyols include propylene glycol, butylene glycol, polyethylene glycol, ethylene glycol, diethylene glycol, triethylene glycol, dipropylene glycol, ethoxydiglycol, pentylene glycol, glycerol, propanediol, butanediol, pentanediol, hexanetriol, and glycerin.

Examples of suitable amides include urea, dimethylacetamide, diethyltoluamide, dimethylformamide (DMF), dimethyloctamide, dimethyldecamide, biodegradable cyclic urea (e.g., 1-alkyl-4-imidazoline-2-one), pyrrolidone derivatives, biodegradable pyrrolidone derivatives (e.g., fatty acid esters of N-(2-hydroxyethyl)-2-pyrrolidone), cyclic amides, hexamethylenelauramide and its derivatives, diethanolamine, and triethanolamine. Examples of pyrrolidone derivatives include 1-methyl-2-pyrrolidone, 2-pyrrolidone, 1-lauryl-2-pyrrolidone, 1-methyl-4-carboxy-2-pyrrolidone, 1-hexyl-4-carboxy-2-pyrrolidone, 1-lauryl-4-carboxy-2-pyrrolidone, 1-methyl-4-methoxycarbonyl-2-pyrrolidone, 1-hexyl-4-methoxycarbonyl-2-pyrrolidone, 1-lauryl-4-methoxycarbonyl-2-pyrrolidone, N-cyclohexylpyrrolidone, N-dimethylaminopropylpyrrolidone, N-cocoalkypyrrolidone, N-tallowalkylpyrrolidone, and N-methylpyrrolidone. Examples of cyclic amides include 1-dodecylazacycloheptane-2-one (e.g., Azone®), 1-geranylazacycloheptan-2-one, 1-farnesylazacycloheptan-2-one, 1-geranylgeranylazacycloheptan-2-one, 1-(3,7-dimethyloctyl)azacycloheptan-2-one, 1-(3,7,11-trimethyldodecyl)azacyclohaptane-2-one, 1-geranylazacyclohexane-2-one, 1-geranylazacyclopentan-2,5-dione, and 1-farnesylazacyclopentan-2-one.

Suitable surfactants may include anionic surfactants, cationic surfactants, nonionic surfactants, bile salts, and lecithin. Examples of suitable anionic surfactants include sodium laurate, sodium lauryl sulfate, and sodium laureth sulfate. Suitable cationic surfactants include cetyltrimethyl ammonium bromide, tetradecyltrimethylammonium bromide, benzalkonium chloride, octadecyltrimethylammonium chloride, cethylpyridinium chloride, dodecyltrimethylammonium chloride, and hexadecyultrimethylammonium chloride. Examples of suitable nonionic surfactants include poloxamer 231, poloxamer 182, poloxamer 184, Brij® 30 (polyoxyethylene (4) lauryl ether), Brij® 93 (polyoxyethylene (2) oleyl ether), Brij® 96 (polyoxyethylene (20) oleyl ether), Brij® 99 (polyoxyl (10) oleyl ether), Span® 20 (sorbitan monolaurate), Span® 40 (sorbitane monopalmitate), Span®60 (sorbitane monostearate), Span® 80 (sorbitane monooleate), Span® 85 (sorbitane trioleate), TWEEN® 20 (polyethylene glycol sorbitan monolaurate; polyoxyethylene (20) sorbitan monolaurate), TWEEN® 40 (polyoxyethylene (20) sorbitan monopalmitate), TWEEN® 60 (polyethylene glycol sorbitan monostearate; polyoxyethylene (20) sorbitan monostearate), TWEEN® 80 (polyethylene glycol sorbitan monooleate; polyoxyethylene (20) sorbitan monooleate), Myrj® 45 (polyoxyethylene (8) stearate), Myrj® 51 (polyoxyethylene stearate), Myrj® 52 (polyoxyethylene stearate), and Miglyol 840 (propylene glycol dicaprylate/dicaprat), among others. Examples of suitable bile salts include sodium cholate, and sodium salts of taurocholic, glycholic, and desoxycholic acids.

Suitable terpenes include hydrocarbons (e.g., D-limonene, α-pinene, β-carene, etc.), alcohols (e.g. α-terpineol, terpinen-4-ol, carvol, etc.), ketones (e.g., carvone, pulegone, piperitone, menthone, etc.), oxides (e.g., cyclohexene oxide, limonene oxide, α-pinene oxide, cyclopentene oxide, 1,8-cineole, etc.), and oils (e.g., ylang ylang, anise, chenopodium, eucalyptus, peppermint, etc.).

Examples of suitable alkanones include N-heptane, N-octane, N-nonane, N-decane, N-undecane, N-dodecane, N-tridecane, N-tetradecane, and N-hexadecane, among others.

Examples of suitable organic acids include salicylic acid and salicylates (including their methyl, ethyl, and propyl glycol derivatives), citric acid, and succinic acid, among others.

Other examples of suitable skin penetration enhancers are known in the art and include, for example, monoglycerides, polyglycosylated glycerides, glyceryl monoethyl ether, polysorbates, beta-cyclodextrin, cyclopentadecalactone, alkyl-2-(N,N-disubstituted amino)-alkanoate ester, 2-(n-nonyl)-1,3-dioxolane, isopropyl myristate, terpinol, menthol, cineol, monoolein, sodium oleate, oleyl oleate, laurylcapram, bisabolol, capaicin, and capsicum. Other examples of suitable skin penetration enhancers and a description of their mechanism of action may be found in Goodman and Barry, "Percutaneous Absorption," in Mechanisms-Methodology-Drug Delivery, 2nd Edition, Bronaugh and Maibach, eds., 1989, pp. 567-593, Marcel Dekker, Inc., NY.

Preferably, the skin penetration enhancer is selected from the group consisting of n-octanol, D-limonene, oleic acid, cineol, isopropyl myristate, monooleate, monoolein, sodium oleate, oleyl oleate, laurylcapram, sodium lauryl sulfate, bisabolol, DMSO, ethanol, propanol, benzyl alcohol, lauryl alcohol, lauric acid, myristic acid, isopropyl palmitate, diisopropyl adipate, dimethyl isosorbide, propylene glycol, butylene glycol, polyethylene glycol, dipropylene glycol, ethoxydiglycol, pentylene glycol, urea, lecithin, sodium laureth sulfate, benzalkonium chloride, poloxamer 231, Brij® 30, Span® 20, Tween® 20, oil (e.g., ylang ylang, eucalyptus, peppermint), salicylic acid, citric acid, menthol, capaicin, capsicum, and combinations thereof. More preferably the skin penetration enhancer is selected from the group consisting of oleic acid, laurocapram, sodium lauryl sulphate, bisabolol, DMSO, ethanol, lauric acid, myristic acid, isopropyl myristate, isopropyl palmitate, diisopropyl adipate, dimethyl isosorbide, propylene glycol, butylene glycol, polyethylene glycol, dipropylene glycol, ethoxydiglycol, pentylene glycol, lecithin, benzalkonium chloride, D-limonone, oil (e.g., ylang ylang, eucalyptus, peppermint), salicylic acid, menthol, capaicin, capsicum, and combinations thereof.

Typically, the compositions of the present disclosure comprise from about 0.01% (by weight of the composition) to about 25% (by weight of the composition) of a skin penetration enhancer, more preferably from about 0.1% (by weight of the composition) to about 15% (by weight of the composition) of a skin penetration enhancer.

The oleocanthal-containing compositions described herein may be employed with one or more conventional pharmaceutically-acceptable and compatible carrier materials useful for the desired application. The carrier can be capable of co-dissolving or suspending the oleocanthal. Carrier materials suitable for use in the instant disclosure include those well-known for use in the cosmetic and medical arts as a basis for ointments, lotions, creams, salves, aerosols, gels, suspensions, sprays, foams, and the like, and may be used in their art-established levels.

Non-limiting examples of suitable carrier materials include water, emollients, sterols or sterol derivatives, natural and synthetic fats or oils, solidifying agents, viscosity enhancers, rheology enhancers, polyols, surfactants, alcohols, esters, silicones, clays, starch, cellulose, and other pharmaceutically acceptable carrier materials. As will be recognized by one skilled in the art, the relative amounts of components in the compositions of the disclosure that can be used to formulate the composition will be dictated by the nature of the composition. The levels can be determined by routine experimentation in view of the disclosure provided herein.

Thus, in one embodiment, the composition of the disclosure can optionally include one or more emollient, which typically acts to soften, soothe, and otherwise lubricate and/or moisturize the skin. Suitable emollients that can be incorporated into the compositions include oils such as petrolatum based oils, petrolatum, vegetable based oils, mineral oils, natural or synthetic oils, alkyl dimethicones, alkyl methicones, alkyldimethicone copolyols, phenyl silicones, alkyl trimethylsilanes, dimethicone, dimethicone crosspolymers, cyclomethicone, lanolin and its derivatives, fatty esters, glycerol esters and derivatives, propylene glycol esters and derivatives, alkoxylated carboxylic acids, alkoxylated alcohols, fatty alcohols, and combinations thereof. The esters can be selected from cetyl palmitate, stearyl palmitate, cetyl stearate, isopropyl laurate, isopropyl myristate, isopropyl palmitate, and combinations thereof. The fatty alcohols include octyldodecanol, lauryl, myristyl, cetyl, stearyl, behenyl alcohol, and combinations thereof. Ethers such as eucalyptol, ceteraryl glucoside, dimethyl isosorbic polyglyceryl-3 cetyl ether, polyglyceryl-3 decyltetradecanol, propylene glycol myristyl ether, and combinations thereof can also suitably be used as emollients.

The composition may desirably include one or more emollient in an amount of from about 0.1% to about 95% by weight, more desirably from about 5% to about 75% by weight, and even more desirably from about 10% to about 50% by weight of the composition.

Stearol and stearol derivatives which are suitable for use in the compositions of the present disclosure include, but are not limited to cholestol, sitosterol, stigmasterol, ergosterol, $C_{10}$-$C_{30}$ cholesterol/lanosterol esters, cholecalciferol, cholesteryl hydroxystearate, cholesteryl isostearate, cholesteryl stearate, 7-dehydrocholesterol, dihydrocholesterol, dihydrocholesteryl octyldecanoate, dihydrolanosterol, dihydrolanosteryl octyidecanoate, ergocalciferol, tall oil sterol, soy sterol acetate, lanasterol, soy sterol, avocado sterols, fatty alcohols, and combinations thereof.

The composition of the invention can desirably include sterols, sterol derivatives or mixtures of both sterols and sterol derivatives in an amount of from about 0.1% to about 10% by weight, more desirably from about 0.5% to about 5% by weight, and even more desirably from about 0.8% to about 1% by weight of the composition.

The compositions of the disclosure can also include natural fats and oils. As used herein, the term "natural fat or oil" is intended to include fats, oils, essential oils, essential fatty acids, non-essential fatty acids, phospholipids, and combinations thereof. These natural fats and oils can provide a source of essential and non-essential fatty acids to those found in the skin's natural barrier. Suitable natural fats or oils can include citrus oil, olive oil, avocado oil, apricot oil, babassu oil, borage oil, camellia oil, canola oil, castor oil, coconut oil, corn oil, cottonseed oil, emu oil, evening primrose oil, hydrogenated cottonseed oil, hydrogenated palm kernel oil, maleated soybean oil, meadowfoam oil, palm kernel oil, peanut oil, rapeseed oil, grapeseed oil, safflower oil, sphingolipids, seed almond oil, tall oil, lauric acid, palmitic acid, stearic acid, linoleic acid, stearyl alcohol, lauryl alcohol, myristyl alcohol, behenyl alcohol, rose hip oil, calendula oil, chamomile oil, eucalyptus oil, juniper oil, sandlewood oil, tea tree oil, sunflower oil, soybean oil, and combinations thereof.

The composition of the invention may desirably include fats and oils in an amount of from about 0.1% to about 95% by weight, more desirably from about 5% to about 75% by weight, and even more desirably from about 10% to about 50% by weight of the composition.

Optionally, the composition may comprise a solidifying agent, which may function to solidify the composition so that the composition is a solid at room temperature, and may affect the hardness and melting point of the composition. The solidifying agent also provides a tackiness to the composition that improves the transfer to the skin of the wearer, such as when the composition is incorporated into a personal care product. Depending on the solidifying agent selected, the solidifying agent can also modify the mode of transfer so that the composition tends to fracture or flake off instead of actually rubbing off onto the skin of the wearer which can lead to improved transfer to the skin. The solidifying agent may further function as an emollient, occlusive agent, and/or moisturizer. The solidifying agents may include waxes as well as compounds that perform functionally as waxes.

The solidifying agents can be selected from alkyl siloxanes, polymers, hydrogenated vegetable oils having a melting point of 35° C. or greater and fatty acid esters with a melting point of 35° C. or greater. Additionally, the solidifying agents can be selected from animal, vegetable and mineral waxes and alkyl silicones. Examples of solidifying agents include, but are not limited to, alkyl trimethylsilanes, beeswax, $C_{24}$-$C_{28}$ alkyl dimethicone, $C_{30}$ alkyl dimethicone, cetyl methicone, stearyl methicone, cetyl dimethicone, stearyl dimethicone, cerotyl dimethicone, candelilla wax, carnauba, cerasin, hydrogenated microcrystalline wax, jojoba wax, microcrystalline wax, lanolin wax, ozokerite, paraffin, spermaceti wax, cetyl esters, behenyl behenate, $C_{20}$-$C_{40}$ alkyl behenate, $C_{12}$-$C_{15}$ lactate, cetyl palmitate, stearyl palmitate, isosteryl behenate, lauryl behenate, stearyl benzoate, behenyl isostearate, cetyl myristate, cetyl octanote, cetyl oleate, cetyl ricinoleate, cetyl stearate, decyl oleate, $diC_{12}$-$C_{15}$ alkyl fumerate, dibehenyl fumerate, myristyl lactate, myristyl lignocerate, myristyl myristate, myristyl stearate, lauryl stearate, octyldodecyl stearate, octyldodecyl stearoyl stearate, olelyl arachidate, oleyl stearate, tridecyl behenate, tridecyl stearate, tridecyl stearoyl stearate, pentaerythrityl tetrabehenate, pentaerythrityl hydrogenated rosinate, pentaerythrityl distearate, pentaerythrityl tetraabeite, pentaerythrityl tetracocoate, pentaerythrityl tetraperlargonate, pentaerythrityl tetrastearate, theylene vinyl acetate, polyethylene, hydrogenated vegetable oil, hydrogenated squalene, squalene, hydrogenated coconut oil, hydrogenated jojoba oil, hydrogenated palm oil, hydrogenated palm kernel oil, hydrogenated olive oil, polyamides, metal stearates and other metal soaps, $C_{30}$-$C_{60}$ fatty alcohols, $C_{20+}$ fatty acids, polypropylene, polystyrene, polybutane, polybutylene terephthalate, polydipentane, zinc stearate, and combinations thereof.

The composition may desirably include one or more solidifying agents in an amount of from about 0.1% to about 95% by weight, more desirably from about 5% to about 75% by weight, and even more desirably from about 10% to about 50% by weight of the composition.

Optionally, one or more viscosity enhancers may be added to the composition to increase the viscosity, to help stabilize the composition, such as when the composition is incorporated into a personal care product, thereby reducing migration of the composition and improve transfer to the skin. Suitable viscosity enhancers include polyolefin resins, lipophilic/oil thickeners, ethylene/vinyl acetate copolymers, polyethylene, silica, silica silylate, silica methyl silylate, colloidal silicone dioxide, cetyl hydroxy ethyl cellulose, other organically modified celluloses, PVP/decane copolymer, PVM/MA decadiene crosspolymer, PVP/eicosene copolymer, PVP/hexadecane copolymer, clays, carbomers, acrylic based thickeners, and combinations thereof.

The composition may desirably include one or more viscosity enhancers in an amount of from about 0.1% to about 25% by weight, more desirably from about 0.5% to about 20% by weight, and even more desirably from about 1% to about 10% by weight of the composition.

The compositions of the disclosure may optionally further comprise rheology enhancers. Rheology enhancers may help increase the melt point viscosity of the composition so that the composition readily remains on the surface of a personal care product and does not substantially migrate into the interior of the product, while substantially not affecting the transfer of the composition to the skin. Additionally, the rheology enhancers help the composition to maintain a high viscosity at elevated temperatures, such as those encountered during storage and transportation.

Suitable rheology enhancers include combinations of alpha-olefins and styrene alone or in combination with mineral oil or petrolatum, combinations of di-functional alpha-olefins and styrene alone or in combination with mineral oil or petrolatum, combinations of alpha-olefins and isobutene alone or in combination with mineral oil or petrolatum, ethylene/propylene/styrene copolymers alone or in combination with mineral oil or petrolatum, butylene/ethylene/styrene copolymers alone or in combination with mineral oil or petrolatum, ethylene/vinyl acetate copolymers, polyethylene polyisobutylenes, polyisobutenes, polyisobutylene, dextrin palmitate, dextrin palmitate ethylhexanoate, stearoyl inulin, stearalkonium bentonite, distearadimonium hectorite, and stearalkonium hectorite, styrene/butadiene/styrene copolymers, styrene/isoprene/styrene copolymers, styrene-ethylene/butylene-styrene copolymers, styrene-ethylene/propylene-styrene copolymers, (styrene-butadiene) n polymers, (styrene-isoprene) n polymers, styrene-butadiene copolymers, and styrene-ethylene/propylene copolymers and combinations thereof. Specifically, rheology enhancers such as mineral oil and ethylene/propylene/styrene copolymers, and mineral oil and butylene/ethylene/styrene copolymers (Versagel blends from Penreco) are particularly preferred. Also, Vistanex (Exxon) and Presperse (Amoco) polymers are particularly suitable rheology enhancers.

The composition of the invention can suitably include one or more rheology enhancer in an amount of from about 0.5% to about 5% percent by weight of the composition.

Examples of suitable polyols, surfactants, and alcohols include those listed above as skin penetration enhancers.

In certain embodiments, the compositions may optionally comprise water. In these embodiments, the compositions can suitably comprise water in an amount of from about 0.1% (by weight of the composition) to about 99% (by weight of the composition), more preferably from about 10% (by weight of the composition) to about 90% (by weight of the composition), and still more preferably from about 30% (by weight of the composition) to about 85% (by weight of the composition).

Optionally, the oleocanthal-containing compositions may be formulated with a polar co-solvent to further increase the permeability of the oleocanthal into the skin. Preferably, the polar co-solvent is fully miscible in the oleocanthal-containing composition, and has a high affinity for the intercellular spaces in the stratum corneum. Without wishing to be bound by any particular theory, it is believed that polar co-solvents with such characteristics are driven by osmosis into the intercellular spaces in the stratum corneum, causing the stratum corneum to swell. In such a swollen state, the intercellular spaces are more liquid-like and disordered, which enables the oleocanthal to more easily diffuse through the stratum corneum. Examples of suitable polar co-solvents for inclusion in the compositions of the present disclosure include, for example, ethanol, propylene glycol, butanol, isopropanol, propanol, isopropyl myristate, isopropyl palmitate, diisopropyl adipate, dimethyl isosorbide, butylene glycol, polyethylene glycol, dipropylene glycol, ethoxydiglycol, pentylene glycol, and combinations thereof. Preferably, the compositions of the present disclosure comprise from about 1% (by weight of the composition) to about 99% (by weight of the composition) of a polar co-solvent.

The compositions of the present disclosure may optionally further comprise ingredients to relieve irritation, such as anti-itch agents. The anti-itch agents may be present in the composition in an amount of from about 0.1% (by weight of the composition) to about 33% (by weight of the composition), more typically, from about 0.5% (by weight of the composition) to about 5% (by weight of the composition). Examples of suitable anti-itch agents are listed below, as well as the preferred concentration for each agent, given in percent by weight of the composition: lauromacrogols, benzocaine (about 5% to about 20%), butamben picrate (about 1%), dibucaine (about 0.25% to about 1%), dibucaine hydrochloric acid (0.25% to about 1%), dimethisoquin hydrochloric acid (about 0.3% to about 0.5%), dyclonine hydrochloric acid (about 0.5% to about 1%), lidocaine (about 0.5% to about 5%), lidocaine hydrochloric acid (about 0.5% to about 5%), pramoxine hydrochloric acid (about 0.5% to about 1%), tetracaine (about 1% to about 2%), tetracaine hydrochloric acid (about 1% to about 2%), benzyl alcohol (about 10% to about 33%), camphor (about 0.1% to about 3%), juniper tar (about 1% to about 5%), menthol (about 0.1% to about 1%), phenol (about 0.5% to about 1.5%), phenolate sodium (about 0.5% to about 1.5%), resorcinol (about 0.5% to about 3%), diphenhydramine hydrochloric acid (about 1% to about 2%), tripelennamine hydrochloric acid (about 0.5% to about 2%), hydrocortisone (about 0.1% to about 5%, preferably about 0.5% to about 2.5%), and combinations thereof. The compositions of the present invention may optionally also comprise cosmetic anti-itch ingredients such as, for example, Symcalmin® (Symrise GmbH & Co., Holzminden, Germany), which is an oat based anti-itch ingredient, also known as "pentylene glycol and butylene glycol and dihydroavenanthramide D". Symcalmin® may be present in the composition in an amount of from about 0.1% (by weight of the composition) to about 2% (by weight of the composition).

Optionally, the compositions may additionally comprise sunscreen actives. Suitable sunscreen actives for inclusion in the compositions of the present disclosure include benzophenone-8, butyl methoxydibenzoymethane, cinoxate, DEA-methoxycinnamate, digalloyl trioleate, 1-(3,4-dimethoxyphenyl)-4,4-dimethyl-1,3-pentanediene, ethyl dihydroxypropyl PABA, ethylhexyl dimethyl PABA, ethylhexyl methoxycinnamate, ethylhexyl salicylate, 4-(2-Beta-Blucopyranosiloxy) propoxy-2-hydroxybenzophenone, glyceryl PABA, homosalate, mentyl anthranilate, octocrylene, PABA, phenylbenzimidazole sulfonic acid, red petrolatum, TEA salicylate, titanium dioxide, zinc oxide, surface treated titanium dioxide, surface treated zinc oxide, Spirulina Platensis Powder, Vitis Vinifera seed extract, Helianthus Annus seed extract, tocopherol, terephthalidene dicamphor sulfonic acid, drometrizole trisiloxane, benzylylidene malonate polysiloxane, diethylhexylbutamido triazone, methylene-bis-benzotriazolyl tetramethylbutylphenol, disodium phenyl dibenzimidazole tetrasulfonate, bis-ethylhexyloxyphenol methoxyphenyl triazine, diethylamino hydroxybenzoyl hexyl benzoate, and combinations thereof.

The compositions of the present disclosure may additionally include adjunct components conventionally found in pharmaceutical compositions in their art-established fashion and at their art-established levels. For example, the compositions may comprise additional compatible pharmaceutically active materials for combination therapy, such as antimicrobials, antioxidants, anti-parasitic agents, antipruritics, antifungals, antiseptic actives, biological actives, astringents, keratolytic actives, local anaesthetics, anti-stinging agents, anti-reddening agents, skin soothing agents, and combinations thereof. Other suitable additives that may be included in the compositions of the present disclosure include colorants, deodorants, fragrances, perfumes, emulsifiers, anti-foaming agents, lubricants, natural moisturizing agents, skin conditioning agents, skin protectants and skin benefit agents (e.g., aloe vera and laponite), solvents, solubilizing agents, suspending agents, wetting agents, humectants, preservatives, propellants, dyes and/or pigments, and combinations thereof.

In one embodiment of the present disclosure, the composition, or one or more components of the composition such as the oleocanthal, may be encapsulated in a shell material prior to being formulated into the composition or introduced into or onto a personal care product. For instance, the microcapsules may be used to gradually release the oleocanthal upon an increase in temperature or physical contact, such as when the composition (or personal care product comprising the composition) is contacted with the skin of a user. Suitable microencapsulation shell materials include cellulose-based polymeric materials (e.g., ethyl cellulose), carbohydrate-based materials (e.g., cationic starches and sugars), polyglycolic acid, polylactic acid, and lactic acid-based aliphatic polyesters, and materials derived therefrom (e.g., dextrins and cyclodextrins) as well as other materials compatible with human tissues.

The microencapsulation shell thickness may vary depending upon the composition's formulation, and is generally manufactured to allow the encapsulated composition or component to be covered by a thin layer of encapsulation material, which may be a monolayer or thicker laminate layer, or may be a composite layer. The microencapsulation layer should be thick enough to resist cracking or breaking of the shell during handling or shipping of the product. The microencapsulation layer should be constructed such that humidity from atmospheric conditions during storage, shipment, or wear will not cause a breakdown of the microencapsulation layer and result in a release of the composition or component.

Microencapsulated compositions or components should be of a size such that the user cannot feel the encapsulated shell on the skin during use. Typically, the capsules have a diameter of no more than about 25 micrometers, and desirably no more than about 10 micrometers. At these sizes, there is no "gritty" or "scratchy" feeling when the composition contacts the skin.

In another aspect, the oleocanthal-containing compositions of the present disclosure may be used in combination with a product, such as a personal care product. More particularly, the composition may be incorporated into or onto a substrate, such as a wipe substrate, an absorbent substrate, a fabric or cloth substrate, or a tissue substrate, among others. In this instance, the substrate may be used to transfer the composition to the skin of the user at the point where the product comes in contact with the skin. Numerous products can be used in combination with the oleocanthal-containing compositions described herein in accordance with the present disclosure to reduce inflammation and/or pain in a user. For example, the oleocanthal-containing compositions may be incorporated into personal care products, such as wipes, absorbent articles, bath tissues, cloths, and patches among others. More particularly, the oleocanthal may be incorporated into wipes such as wet wipes, dry wipes, hand wipes, face wipes, cosmetic wipes, and the like, absorbent articles (in particular medical wraps and bandages), patches such as eye patches and dermal patches, cloth material such as spa gloves and socks, headbands, wristbands, helmet pads, and the like.

Although discussed primarily in combination with a wipe substrate, it should be understood that the oleocanthal-containing compositions can also be used in combination with other numerous personal care products, such as those described above. Materials suitable for use as the substrate of the wipe are well known to those skilled in the art, and typically include a fibrous sheet material, which may be either woven or nonwoven. For example, the wipes incorporating the oleocanthal described herein to reduce inflammation and/or pain may include nonwoven fibrous sheet materials, which include meltblown, coform, air-laid, bonded-carded web materials, hydroentangled materials, and combinations thereof. Such materials can be comprised of synthetic or natural fibers, or a combination thereof. Typically, wipes define a basis weight of from about 25 to about 120 grams per square meter and desirably from about 40 to about 90 grams per square meter.

In a particular embodiment, the wipes incorporating the oleocanthal compositions described herein comprise a coform basesheet of polymeric microfibers and cellulosic fibers having a basis weight of from about 60 to about 80 grams per square meter and desirably about 75 grams per square meter. Such coform basesheets are manufactured generally as described in U.S. Pat. No. 4,100,324, which is incorporated by reference. Typically, such coform basesheets comprise a gas-formed matrix of thermoplastic polymeric meltblown microfibers, such as, for example, polypropylene microfibers, and cellulosic fibers, such as, for example, wood pulp fibers.

The relative percentages of the polymeric microfibers and cellulosic fibers in the coform basesheet can vary over a wide range depending upon the desired characteristics of the wipes. For example, the coform basesheet may comprise from about 20 to about 100 weight percent, desirably from about 20 to about 60 weight percent, and more desirably from about 30 to about 40 weight percent of the polymeric microfibers based on the dry weight of the coform basesheet being used to provide the wipes.

Alternatively, the wipes incorporating the oleocanthal compositions described herein can comprise a composite, which includes multiple layers of materials such as those described in U.S. Pat. No. 6,028,018, which is incorporated by reference. For example, the wipes may include a three layer composite, which includes an elastomeric film or meltblown layer between two coform layers as described above. In such a configuration, the coform layers may define a basis weight of from about 15 to about 30 grams per square meter and the elastomeric layer may include a film material such as a polyethylene metallocene film.

As mentioned above, one type of wipe suitable for use in combination with the oleocanthal compositions described herein to reduce inflammation and/or pain include wet wipes, which, in addition to the wipe substrate, comprise a liquid solution or formulation. The liquid solution or formulation can be any liquid, which can be absorbed into the wet wipe basesheet and may include any suitable components, which provide the desired wiping properties. For example, the components may include water, emollients, surfactants, fragrances, preservatives, chelating agents, pH buffers, or combinations thereof as are well known to those skilled in the art. Further, the liquid may also contain lotions, medicaments, and/or antimicrobials.

The amount of liquid contained within each wet wipe may vary depending upon the type of material being used to provide the wet wipe, the type of liquid being used, the type of container being used to store the wet wipes, and the desired end use of the wet wipe. Generally, each wet wipe can contain from about 150 to about 600 weight percent and desirably from about 250 to about 450 weight percent liquid based on the dry weight of the wipe for improved wiping. In a particular aspect, the amount of liquid contained within the wet wipe is from about 300 to about 400 weight percent and desirably about 330 weight percent based on the dry weight of the wet wipe. If the amount of liquid is less than the above-identified ranges, the wet wipe may be too dry and may not adequately perform. If the amount of liquid is greater than the above-identified ranges, the wet wipe may be oversaturated and soggy and the liquid may pool in the bottom of the container.

Each wet wipe is generally rectangular in shape and may have any suitable unfolded width and length. For example, the wet wipe may have an unfolded length of from about 2.0 to about 80.0 centimeters and desirably from about 10.0 to about 25.0 centimeters and an unfolded width of from about 2.0 to about 80.0 centimeters and desirably from about 10.0 to about 25.0 centimeters. Typically, each individual wet wipe is arranged in a folded configuration and stacked one on top of the other to provide a stack of wet wipes. Such folded configurations are well known to those skilled in the art and include c-folded, z-folded, quarter-folded configurations and the like. The stack of folded wet wipes may be placed in the interior of a container, such as a plastic tub, to provide a package of wet wipes for eventual sale to the consumer. Alternatively, the wet wipes may include a continuous strip of material which has perforations between each wipe and which may be arranged in a stack or wound into a roll for dispensing.

In one embodiment of the present disclosure, the oleocanthal-containing compositions are introduced into or onto a fibrous wipe substrate, absorbent substrate, a fabric or cloth substrate, or a tissue substrate. When the substrate contacts the skin of the user, the composition contacts the skin, and may be actually transferred to the skin, whereupon it may be absorbed into skin to reduce inflammation and/or pain in the user. In a specific embodiment, the oleocanthal is introduced into the liquid formulation of a wet wipe.

The oleocanthal compositions described herein may be applied to the substrate using any conventional methods, such as dipping, spraying, printing, coating, extrusion, ink jet printing, and combinations thereof. Preferably, the composition is introduced onto the substrate in an amount of from about 50% by weight of the substrate to about 1000% by weight of the substrate, desirably from about 100% by weight of the substrate to about 500% by weight of the substrate, and more desirably from about 150% by weight of the substrate to about 300% by weight of the substrate.

In one preferred embodiment, oleocanthal may be incorporated into a transdermal patch. Methods for preparing transdermal patches are well known in the art. In one particular example, the patch may be a laminated composite, which contains one or more drug reservoir layers (containing the oleocanthal), a backing layer, and optionally one or more additional layers (e.g., additional drug reservoir layers and/or a strippable protective release liner).

The backing layer, which may be adhered to the drug reservoir layer, serves as the upper layer of the patch during use, and functions as the primary structural element of the patch. The backing layer is made of a sheet or film of a preferably flexible elastomeric material that is substantially impermeable to the oleocanthal or oleocanthal composition. The thickness of the layer is not particularly limited and can be appropriately chosen depending on the application, but will typically be on the order of 1.0 to about 4.0 millimeters in thickness. Preferably, the backing layer is composed of a material that permits the patch to follow the contours of the skin, such that it may be worn comfortably on any skin area, e.g., at joints or other points of flexure. In this way, in response to normal mechanical strain, there is little or no likelihood of the patch disengaging from the skin due to differences in the flexibility or resiliency of the skin and the patch. Examples of polymers useful for the backing layer include polyethylene, polypropylene, polyesters, polyurethanes, polyvinyl chloride, polyethylene vinyl acetate, polyvinylidene chloride, block copolymers, nylon, an unwoven fabric, and the like. The backing layer may also comprise laminates of one or more of the foregoing polymers.

The drug reservoir layer typically comprises a contact adhesive which is a pressure-sensitive adhesive suitable for long-term skin contact. The adhesive is preferably also physically and chemically compatible with the oleocanthal and with any carriers or vehicles incorporated into an oleocanthal composition. Further, the adhesive selected for use in the reservoir layer is preferably such that the oleocanthal is at least somewhat soluble in the adhesive. The thickness of the drug reservoir layer is not particularly limited, but will generally be in the range of about 2 to about 4 millimeters in thickness. Suitable adhesives for use in the drug reservoir include polysiloxanes, polyacrylates, polyurethanes, tacky rubbers such as polyisobutylene, and the like. Particularly preferred contact adhesives for use in the drug reservoir herein are cross-linked acrylates.

The adhesive is typically gelled with oleocanthal or an oleocanthal-containing composition to form the drug reservoir layer. Advantageously, it has been discovered that the transdermal patch, and in particular the drug reservoir layer, may also be constructed using materials that disrupt the stratum corneum, thus facilitating transport of the oleocanthal through the stratum corneum. In particular, the drug reservoir layer of the patch may comprise short, stiff, fibers, such as hollow fibers, microfibers, nanofibers, and combinations thereof, gelled in a solution containing oleocanthal. Preferably, the fibers are sufficiently sharp that they are able to penetrate, at least partially, the stratum corneum, thus allowing passage of the oleocanthal through the stratum corneum.

In one embodiment, the fibers are hollow fibers. Preferably, the hollow fibers have a submicron diameter, but are several microns in length (i.e., have a length sufficient to penetrate at least partially into the stratum corneum). In certain embodiments, the fibers have a diameter of from about 0.1 µm to about 10 µm, more preferably from about 0.2 µm to about 5 µm, and have a length of from about 1 µm to about 100 µm, and more preferably from about 2 µm to about 25 µm. Examples of suitable fibers include, but are not limited to, hollow keratin fibers, carbon nanotubes, wood pulp fiber, processed wood pulp fibers, glass hollow fibers, ceramic fibers (e.g., from aluminum oxides), and fibrous minerals such as sepiolite, attapulgite, and the like. A number of suitable fibers are commercially available, for example, from Engelhard (Iselin, N.J.) and Dupont.

The fibers may be gelled with oleocanthal, and optionally suitable carrier materials, additional skin penetration enhancers, polar co-solvents, such as those described above, and/or adhesives to form the drug reservoir layer. Preferably, this composition comprises from about 5% (by weight) to about 50% (by weight) fibers, and more preferably from about 10% (by weight) to about 35% (by weight) fibers. Typically, the composition will comprise oleocanthal in an amount effective to reduce inflammation and/or pain, and preferably at least about 0.04% (by weight of the composition) of oleocanthal, more preferably from about 0.04% (by weight of the composition) to about 10.0% (by weight of the composition) of oleocanthal, more preferably from about 0.10% (by weight of the composition) to about 5.0% (by weight of the composition) of oleocanthal, and still more preferably about 0.50% (by weight of the composition) of oleocanthal. Optionally, the composition may further comprise skin penetration enhancers, polar co-solvents, anti-itch ingredients, and the like, in suitable amounts, such as those described herein. In certain embodiments, the drug reservoir layer may further comprise additional suitable carrier materials, such as those described herein. Optionally, an adhesive, such as those described above, may be included in the composition in any suitable amount, for example, about 10% (by weight) or less.

In one particularly preferred embodiment, the composition comprises from about 10% to about 50% (by weight) hollow fibers, from about 0.04% (by weight of the composition) to about 10.0% (by weight of the composition) of oleocanthal, and from about 0.01% (by weight of the composition) to about 25% (by weight of the composition) of a skin penetration enhancer.

Preferably, the fibers, the oleocanthal, and optionally the adhesive, skin penetration enhancers, polar co-solvents, and/or carrier materials are gelled together to form the drug reservoir layer. For example, these components may be combined with water soluble polymeric substances suitable for forming a gel. Examples of suitable water soluble polymeric substances include, for example, gelatin, starch, agar, mannan, alginic acid, polyacrylic acid, dextrin, methyl cellulose, hydroxypropyl cellulose, methyl cellulose sodium, carboxymethyl cellulose, carboxymethyl cellulose sodium, polyvinyl alcohol, polyvinyl pyrolidone, methyl vinyl ether-maleic anhydride copolymer, gum Arabic, gum tragacanth, karaya gum, locust bean gum, and the like. Preferably, the water soluble polymeric materials included in the drug reservoir layer are present in an amount from about 0.5% to about 50% by weight of the composition and more preferably from about 5% to about 25% by weight of the composition.

Optionally, the gelled composition may further comprise water, which aids in swelling the stratum corneum and further improves the penetration of the oleocanthal through the skin. Preferably, the amount of water in the gelled composition is from about 10% to about 80% by weight of the composition, and more preferably is from about 20% to about 60% by weight of the composition. Optionally, the gelled composition may further comprise a fully miscible co-solvent. Preferably, the co-solvent has a polarity lower than water, such as, for example, 1-butanol. Inclusion of such a co-solvent may aid in penetration of the water into the stratum corneum, thus enhancing the swelling effect.

Optionally, the patch may further comprise a release liner. The release liner is a disposable element which serves to protect the patch prior to application. Typically, the release liner is formed from a material impermeable to the oleocanthal, any carriers or vehicles, and adhesive, and is easily stripped from the contact adhesive that serves as part of the drug reservoir layer. Preferred release liners for use herein are those which are generally suitable for use in conjunction with pressure-sensitive adhesives, such as silanized polyester films, among others.

In general, the patches are fabricated using methods standard in the art. For example, the patch may be prepared by spreading and coating the oleocanthal/adhesive composition onto an appropriate substrate (e.g., the backing layer or the release liner) to form a drug reservoir layer. Other layers may then be laminated to this initial structure.

The patch may be applied directly to the skin of a user. Advantageously, the penetration of the oleocanthal into the skin and through the stratum corneum is enhanced by the presence of the hollow fibers in the drug reservoir layer. In certain instances, the hollow interior of the fibers may act as a reservoir for the oleocanthal, thus allowing slow, continuous release of the oleocanthal to the user.

Having described the disclosure in detail, it will be apparent that modifications and variations are possible without departing from the scope of the disclosure defined in the appended claims.

EXAMPLES

The following non-limiting examples are provided to further illustrate the present disclosure.

Example 1

Oleocanthal Spray

In this example, an oleocanthal-containing spray is produced. The following ingredients are used to prepare the oleocanthal spray.

TABLE 1

| Phase | Trade Name | Common Name | Function | % weight | grams |
|---|---|---|---|---|---|
| A | Water | Water | Carrier | 45.80 | 366.40 |
| B | Hydrolite-5 | Pentylene glycol | Carrier/anti microbial | 5.00 | 40.00 |
| B | Transcutol CG | Ethoxydiglycol | Penetration enhancer | 5.00 | 40.00 |
| B | Arlasolve DMI | Dimethyl isosorbide | Penetration enhancer | 5.00 | 40.00 |
| B | SD alcohol 40B | SD alcohol 40B | Carrier/co-solvent | 35.00 | 280.00 |
| B | Symcalmin ® (Symrise GmbH & Co., Holzminden, Germany) | Pentylene glycol and butylene glycol and dihydro-avenanthramide D | Anti-itch/penetration enhancer | 0.50 | 4.00 |
| B | Oleocanthal | Oleocanthal | Active ingredient | 0.50 | 4.00 |
| C | Glucam E-20 (Amerchol) | Methyl gluceth-20 | Emollient/humectant | 3.00 | 24.00 |
| C | Fragrance | Fragrance | Fragrance | 0.20 | 1.60 |
| D | Citric acid or NaOH | Citric acid or NaOH | pH adjustment | As needed | As needed |

The oleocanthal spray is prepared by mixing the phase B ingredients at room temperature until clear. The Phase A ingredient (water) is then added, and the solution is mixed until homogenous. The Phase C ingredients are first premixed, and then added to the solution, and the resulting solution is again mixed until homogenous. The pH of the spray is adjusted to about 5.0 to about 6.0, using citric acid and/or NaOH, as needed.

Example 2

Anhydrous Oleocanthal Base

In this example, an anhydrous oleocanthal base is produced. The base is prepared by mixing the ingredients listed in Table 2 until homogenous.

TABLE 2

| Ingredient | Function | % weight | grams |
|---|---|---|---|
| Petrolatum | Carrier | 89.00 | 445.00 |
| Mineral oil | Emollient | 10.00 | 50.00 |
| Oleocanthal | Active ingredient | 0.50 | 2.50 |
| Bisabolol | Penetration enhancer | 0.50 | 2.50 |

The resulting oleocanthal base may be used to produce various oleocanthal-containing emulsions, creams, and ointments.

Example 3

Oleocanthal Cream

In this example, an oleocanthal-containing cream is produced. The following ingredients are used to prepare the oleocanthal cream.

The oleocanthal cream is prepared by mixing the Phase 1 ingredients at a temperature of 75° C. at a speed of about 400 rpm until homogenous. The Phase 2 ingredients are separately mixed at a speed of about 400 rpm and at a temperature of 75° C. until homogenous. The Phase 1 and Phase 2 mixtures are then combined, and further mixed at about 800 rpm for 5 minutes. The resulting mixture is neutralized with the Phase 3 ingredient (KOH 10%) to a pH of about 6.0. The mixture is homogenized for 1 minute with mixing at about

TABLE 3

| Phase | Trade Name | Common Name | Function | Amount % weight | Amount grams |
|---|---|---|---|---|---|
| 1 | Water | Water | Carrier | 69.60 | 556.80 |
| 1 | Carbopol ® Ultrez 10 (Noveon, Inc., Cleveland, OH) | Carbomer | Rheology modifier | 0.35 | 2.80 |
| 1 | Tic ® prehydrated xanthan gum (Tic Gums, Belcamp, MD) | Xanthan gum | Rheology modifier | 0.10 | 0.80 |
| 1 | Versene ® $Na_2$ (The Dow Chemical Company, Midland, MI) | Disodium EDTA | Chelating agent | 0.10 | 0.80 |
| 1 | Germazide ® C (Engelhard, Corp., Iselin, NJ) | Chlorphenesin | Preservative | 0.20 | 1.60 |
| 1 | Glycerin | Glycerin | Humectant | 3.00 | 24.00 |
| 1 | Transcutol CG | Ethoxydiglycol | Penetration enhancer | 5.00 | 40.00 |
| 2 | Arlacel 165 | Glyceryl stearate & PEG-100 stearate | Emulsifier | 3.00 | 24.00 |
| 2 | CUPL ® Pic (Bernel Chemical Co., Englewood, NJ) | PPG-2-isoceteth-3 acetate | Emulsifier | 1.00 | 8.00 |
| 2 | Cetyl alcohol | Cetyl alcohol | Solidifying agent | 2.50 | 20.00 |
| 2 | Emerest ® 2400 (Emerest Industries, Cincinnati, OH) | Glyceryl stearate | Solidifying agent | 1.00 | 8.00 |
| 2 | Stearic acid | Stearic acid | Solidifying agent | 1.00 | 8.00 |
| 2 | Petrolatum | Petrolatum | Emollient | 3.00 | 24.00 |
| 2 | Drakeol ® 7 (Penreco, Houston, TX) | Mineral oil | Emollient | 3.00 | 24.00 |
| 2 | Neobee ® M-5 (Stepan, Co., Northfield, IL) | Caprylic/capric triglyceride | Emollient | 2.00 | 16.00 |
| 2 | Elefac I-205 (Bernel Chemical Co., Englewood, NJ) | Octododecanonal neopentanoate | Emollient | 1.25 | 10.00 |
| 3 | KOH 10% | Potassium hydroxide | pH adjustment | 1.80 | 14.40 |
| 4 | DC 200 350 cst (Dow Corning) | Dimethicone | Emollient | 0.40 | 3.20 |
| 5 | Oleocanthal | Oleocanthal | Active ingredient | 0.50 | 4.00 |
| 5 | SymCalmin ® (Symrise GmbH & Co., Holzminden, Germany) | Pentylene glycol and butylene glycol and dihydro-avenanthramide D | Anti-itch | 0.50 | 4.00 |
| 5 | Mackadet MEPB | Phenoxyethanol, methylparaben, ethylparaben, propylparaben | Preservative | 0.70 | 5.60 |

4000 rpm. The mixture is cooled to 40° C., with mixing at about 800 rpm. During cooling, when the temperature of the mixture reaches about 55 to 60° C., the Phase 4 ingredient is added, with mixing at about 800 rpm. The Phase 5 ingredients are separately mixed, while warming to 40° C., until clear. The Phase 5 ingredients are added to the cooled mixture at 40° C. The resulting mixture is cooled to room temperature. The pH of the cream is adjusted to about 6.5, using KOH, as needed.

It is to be understood that the mixing speeds described herein are illustrative only, and actual mixing speeds may vary from those given depending on batch size and temperature of the mixture. Appropriate mixing speeds may be readily determined by one skilled in the art.

When introducing elements of the present disclosure or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the disclosure are achieved and other advantageous results attained.

As various changes could be made in the above compositions and methods without departing from the scope of the disclosure, it is intended that all matter contained in the above description shall be interpreted as illustrative and not in a limiting sense.

What is claimed is:

1. A topical composition for relief of inflammation, the topical composition comprising a pharmaceutically acceptable carrier, at least about 0.04% (by weight of the composition) of oleocanthal, and an anti-itch agent in an amount of from about 0.1% (by weight of the composition) to about 33% (by weight of the composition), wherein the anti-itch agent is selected from the group consisting of lauromacrogols, benzocaine, butamben picrate, dibucaine, dibucaine hydrochloric acid, dyclonine hydrochloric acid, lidocaine, lidocaine hydrochloric acid, pramoxine hydrochloric acid, tetracaine, tetracaine hydrochloride, camphor, juniper tar, menthol, phenol, phenolate sodium, resorcinol, diphenhydramine hydrochloric acid, tripelennamine hydrochloric acid, hydrocortisone, pentylene glycol, butylene glycol, dihydroavenanthramide D, and combinations thereof.

2. The topical composition of claim 1 wherein the topical composition comprises from about 0.04% (by weight of the composition) to about 10.0% (by weight of the composition) of oleocanthal.

3. The topical composition of claim 1 wherein the topical composition further comprises a skin penetration enhancer.

4. The topical composition of claim 3 wherein the skin penetration enhancer is selected from the group consisting of dimethylsulfoxide, decylmethylsulfoxide, ethanol, propanol, butanol, pentanol, hexanol, octanol, n-octanol, nonanol, decanol, 2-butanol, 2-pentanol, benzyl alcohol, caprylic alcohol, decyl alcohol, lauryl alcohol, 2-lauryl alcohol, myristyl alcohol, cetyl alcohol, stearyl alcohol, oleyl alcohol, linoleyl alcohol, linolenyl alcohol, isopropyl alcohol, valeric acid, heptanoic acid, pelagonic acid, caproic acid, capric acid, lauric acid, myristic acid, stearic acid, oleic acid, caprylic acid, isovaleric acid, neopentanoic acid, neoheptanoic acid, neononanoic acid, trimethyl hexanoic acid, neodecanoic acid, isostearic acid, isopropyl n-butyrate, isopropyl n-hexanoate, isopropyl n-decanoate, isopropyl miristate, isopropyl palmitate, octyldodecyl myristate, ethyl acetate, butyl acetate, methyl acetate, methylvalerate, methylpropionate, diethyl sebacate, ethyl oleate, diisopropyl adipate, dimethyl isosorbide, propylene glycol, butylene glycol, polyethylene glycol, ethylene glycol, diethylene glycol, triethylene glycol, dipropylene glycol, ethoxydiglycol, pentylene glycol, glycerol, propanediol, butanediol, pentanediol, hexanetriol, glycerin, urea, dimethylacetamide, diethyltoluamide, dimethylformamide, dimethyloctamide, dimethyldecamide, 1-alkyl-4-imidazoline-2-one, fatty acid esters of N-(2-hydroxyethyl)-2-pyrrolidone, cyclic amides, hexamethylenelauramide, diethanolamine, triethanolamine, 1-methyl-2-pyrrolidone, 2-pyrrolidone, 1-lauryl-2-pyrrolidone, 1-methyl-4-carboxy-2-pyrrolidone, 1-hexyl-4-carboxy-2-pyrrolidone, 1-lauryl-4-carboxy-2-pyrrolidone, 1-methyl-4-methoxycarbonyl-2-pyrrolidone, 1-hexyl-4-methoxycarbonyl-2-pyrrolidone, 1-lauryl-4-methoxycarbonyl-2-pyrrolidone, N-cyclohexylpyrrolidone, N-dimethylaminopropylpyrrolidone, N-cocoalkypyrrolidone, N-tallowalkylpyrrolidone, N-methylpyrrolidone, 1-dodecylazacycloheptane-2-one, 1-geranylazacycloheptan-2-one, 1-farnesylazacycloheptan-2-one, 1-geranylgeranylazacycloheptan-2-one, 1-(3,7-dimethyloctyl)azacycloheptan-2-one, 1-(3,7,11-trimethyldodecyl)azacyclohaptane-2-one, 1-geranylazacyclohexane-2-one, 1-geranylazacyclopentan-2,5-dione, 1-farnesylazacyclopentan-2-one, lecithin, sodium laurate, sodium lauryl sulfate, sodium laureth sulfate, cetyltrimethyl ammonium bromide, tetradecyltrimethylammonium bromide, benzalkonium chloride, octadecyltrimethylammonium chloride, cethylpyridinium chloride, dodecyltrimethylammonium chloride, hexadecyultrimethylammonium chloride, poloxamer 231, poloxamer 182, poloxamer 184, polyoxyethylene (4) lauryl ether, polyoxyethylene (2) oleyl ether, polyoxyethylene (20) oleyl ether, polyoxyl (10) oleyl ether, sorbitan monolaurate, sorbitane monopalmitate, sorbitane monostearate, sorbitane monooleate, sorbitane trioleate, polyoxyethylene (20) sorbitan monolaurate, polyoxyethylene (20) sorbitan monopalmitate, polyoxyethylene (20) sorbitan monostearate, polyoxyethylene (20) sorbitan monooleate, polyoxyethylene (8) stearate, polyoxyethylene stearate, propylene glycol dicaprylate/dicaprat, sodium cholate, sodium salts of taurocholic, glycholic, and desoxycholic acids, D-limonone, ÿ-pinene, ÿ-carene, ÿ-terpineol, terpinen-4-ol, carvol, carvone, pulegone, piperitone, menthone, cyclohexene oxide, limonene oxide, ÿ-pinene oxide, cyclopentene oxide, 1,8-cineole, ylang ylang oil, anise, chenopodium, eucalyptus oil, peppermint oil, N-heptane, N-octane, N-nonane, N-decane, N-undecane, N-dodecane, N-tridecane, N-tetradecane, N-hexadecane, salicylic acid, salicylates, citric acid, succinic acid, monoglycerides, polyglycosylated glycerides, glyceryl monoethyl ether, polysorbates, ÿ-cyclodextrin, cyclopentadecalactone, alkyl-2-(N,N-disubstituted amino)-alkanoate ester, 2-(n-nonyl)-1,3-dioxolane, isopropyl myristate, terpinol, menthol, cineol, monoolein, sodium oleate, oleyl oleate, laurylcapram, bisabolol, capaicin, capsicum, and combinations thereof.

5. The topical composition of claim 3 wherein the topical composition comprises from about 0.01% (by weight of the composition) to about 25% (by weight of the composition) of the skin penetration enhancer.

6. The topical composition of claim 1 further comprising a polar co-solvent.

7. A personal care product comprising a substrate and the topical composition of claim 1.

8. The personal care product of claim 7 wherein the personal care product is selected from the group consisting of a wipe and an absorbent article.

9. The personal care product of claim 7 wherein the personal care product comprises from about 50% (by weight of the substrate) to about 1000% (by weight of the substrate) of the topical composition.

10. A topical composition for relief of inflammation, the topical composition comprising a pharmaceutically acceptable carrier, oleocanthal, a skin penetration enhancer, and an anti-itch agent in an amount of from about 0.1% (by weight of the composition) to about 33% (by weight of the composition), wherein the anti-itch agent is selected from the group consisting of lauromacrogols, benzocaine, butamben picrate, dibucaine, dibucaine hydrochloric acid, dyclonine hydrochloric acid, lidocaine, lidocaine hydrochloric acid, pramoxine hydrochloric acid, tetracaine, tetracaine hydrochloric acid, camphor, juniper tar, menthol, phenol, phenolate sodium, resorcinol, diphenhydramine hydrochloric acid, tripelennamine hydrochloric acid, hydrocortisone, pentylene glycol, butylene glycol, dihydroavenanthramide D, and combinations thereof.

11. The topical composition of claim 10 wherein the topical composition comprises from about 0.04% (by weight of the composition) to about 10.0% (by weight of the composition) of oleocanthal.

12. The topical composition of claim 10 wherein the skin penetration enhancer is selected from the group consisting of dimethylsulfoxide, decylmethylsulfoxide, ethanol, propanol, butanol, pentanol, hexanol, octanol, n-octanol, nonanol, decanol, 2-butanol, 2-pentanol, benzyl alcohol, caprylic alcohol, decyl alcohol, lauryl alcohol, 2-lauryl alcohol, myristyl alcohol, cetyl alcohol, stearyl alcohol, oleyl alcohol, linoleyl alcohol, linolenyl alcohol, isopropyl alcohol, valeric acid, heptanoic acid, pelagonic acid, caproic acid, capric acid, lauric acid, myristic acid, stearic acid, oleic acid, caprylic acid, isovaleric acid, neopentanoic acid, neoheptanoic acid, neononanoic acid, trimethyl hexanoic acid, neodecanoic acid, isostearic acid, isopropyl n-butyrate, isopropyl n-hexanoate, isopropyl n-decanoate, isopropyl miristate, isopropyl palmitate, octyldodecyl myristate, ethyl acetate, butyl acetate, methyl acetate, methylvalerate, methylpropionate, diethyl sebacate, ethyl oleate, diisopropyl adipate, dimethyl isosorbide, propylene glycol, butylene glycol, polyethylene glycol, ethylene glycol, diethylene glycol, triethylene glycol, dipropylene glycol, ethoxydiglycol, pentylene glycol, glycerol, propanediol, butanediol, pentanediol, hexanetriol, glycerin, urea, dimethylacetamide, diethyltoluamide, dimethylformamide, dimethyloctamide, dimethyldecamide, 1-alkyl-4-imidazoline-2-one, fatty acid esters of N-(2-hydroxyethyl)-2-pyrrolidone, cyclic amides, hexamethylenelauramide, diethanolamine, triethanolamine, 1-methyl-2-pyrrolidone, 2-pyrrolidone, 1-lauryl-2-pyrrolidone, 1-methyl-4-carboxy-2-pyrrolidone, 1-hexyl-4-carboxy-2-pyrrolidone, 1-lauryl-4-carboxy-2-pyrrolidone, 1-methyl-4-methoxycarbonyl-2-pyrrolidone, 1-hexyl-4-methoxycarbonyl-2-pyrrolidone, 1-lauryl-4-methoxycarbonyl-2-pyrrolidone, N-cyclohexylpyrrolidone, N-dimethylaminopropylpyrrolidone, N-coalkypyrrolidone, N-tallowalkylpyrrolidone, N-methylpyrrolidone, 1-dodecylazacycloheptane-2-one, 1-geranylazacycloheptan-2-one, 1-farnesylazacycloheptan-2-one, 1-geranylgeranylazacycloheptan-2-one, 1-(3,7-dimethyloctyl)azacycloheptan-2-one, 1-(3,7,11-trimethyldodecyl)azacyclohaptane-2-one, 1-geranylazacyclohexane-2-one, 1-geranylazacyclopentan-2,5-dione, 1-farnesylazacyclopentan-2-one, lecithin, sodium laurate, sodium lauryl sulfate, sodium laureth sulfate, cetyltrimethyl ammonium bromide, tetradecyltrimethylammonium bromide, benzalkonium chloride, octadecyltrimethylammonium chloride, cethylpyridinium chloride, dodecyltrimethylammonium chloride, hexadecyultrimethylammonium chloride, poloxamer 231, poloxamer 182, poloxamer 184, polyoxyethylene (4) lauryl ether, polyoxyethylene (2) oleyl ether, polyoxyethylene (20) oleyl ether, polyoxyl (10) oleyl ether, sorbitan monolaurate, sorbitane monopalmitate, sorbitane monostearate, sorbitane monooleate, sorbitane trioleate, polyoxyethylene (20) sorbitan monolaurate, polyoxyethylene (20) sorbitan monopalmitate, polyoxyethylene (20) sorbitan monostearate, polyoxyethylene (20) sorbitan monooleate, polyoxyethylene (8) stearate, polyoxyethylene stearate, propylene glycol dicaprylate/dicaprat, sodium cholate, sodium salts of taurocholic, glycholic, and desoxycholic acids, D-limonone, ÿ-pinene, ÿ-carene, ÿ-terpineol, terpinen-4-ol, carvol, carvone, pulegone, piperitone, menthone, cyclohexene oxide, limonene oxide, ÿ-pinene oxide, cyclopentene oxide, 1,8-cineole, ylang ylang oil, anise, chenopodium, eucalyptus oil, peppermint oil, N-heptane, N-octane, N-nonane, N-decane, N-undecane, N-dodecane, N-tridecane, N-tetradecane, N-hexadecane, salicylic acid, salicylates, citric acid, succinic acid, monoglycerides, polyglycosylated glycerides, glyceryl monoethyl ether, polysorbates, ÿ-cyclodextrin, cyclopentadecalactone, alkyl-2-(N,N-disubstituted amino)-alkanoate ester, 2-(n-nonyl)-1,3-dioxolane, isopropyl myristate, terpinol, menthol, cineol, monoolein, sodium oleate, oleyl oleate, laurylcapram, bisabolol, capaicin, capsicum, and combinations thereof.

13. The topical composition of claim 10 wherein the topical composition comprises from about 0.01% (by weight of the composition) to about 25% (by weight of the composition) of the skin penetration enhancer.

14. The topical composition of claim 10 further comprising a polar co-solvent.

15. A personal care product comprising a substrate and the topical composition of claim 10.

16. The personal care product of claim 15 wherein the personal care product is selected from the group consisting of a wipe and an absorbent article.

17. The personal care product of claim 15 wherein the personal care product comprises from about 50% (by weight of the substrate) to about 1000% (by weight of the substrate) of the topical composition.

* * * * *